United States Patent [19]

Bennett et al.

[11] Patent Number: 5,338,546
[45] Date of Patent: Aug. 16, 1994

[54] TISSUE PLASMINOGEN ACTIVATOR VARIANTS WITH DECREASED CLEARANCE

[75] Inventors: William F. Bennett, San Mateo; Bruce A. Keyt, Pacifica; Mark J. Zoller, San Francisco, all of Calif.

[73] Assignee: Genentech, Inc., So. San Francisco, Calif.

[21] Appl. No.: 33,612

[22] Filed: Mar. 16, 1993

Related U.S. Application Data

[63] Continuation of Ser. No. 912,040, Jul. 9, 1992, Pat. No. 5,246,850, which is a continuation of Ser. No. 560,515, Jul. 31, 1990, abandoned.

[51] Int. Cl.$^5$ .................. C12N 9/64; C12N 15/00; A61K 37/547
[52] U.S. Cl. ................. 424/94.64; 424/94.63; 435/212; 435/226
[58] Field of Search .......... 435/226, 212, 219; 424/94.63, 94.64

[56] References Cited

FOREIGN PATENT DOCUMENTS

| 0241208 | 6/1987 | European Pat. Off. . |
| 0240334 | 10/1987 | European Pat. Off. . |
| WO84/01960 | 5/1984 | PCT Int'l Appl. . |
| WO86/01538 | 3/1986 | PCT Int'l Appl. . |
| WO8911531 | 11/1989 | PCT Int'l Appl. . |

OTHER PUBLICATIONS

Collen et al., *J. Biol. Chem.* 265, 12183 (1990).
JP-A-63230083 [Patent Abstracts of Japan 12(24), c-561, 3372, Jan. 19, 1989].
Zoller et al., *Faseb Journal* 4, A1695 (1990).
Bennett et al., *J. Biol. Chem.* 226, 5191 (1991).
Kalyan et al *J. Biol. Chem.* 263:3971–3978 (1988).
Hotchkiss et al *Thromb. Haemost.* 60:255 (1988).
Cambier et al. *J. Cardiovasc. Pharmacol.* 11:468 (1988).
Higgins & Bennett *Annu. Rev. Pharmacol. Toxicol* 30:91–212 (1990).
Gardell, S. J. et al., *J. Biol. Chem.* 264(30); 17947–52 (1989).
Ny, T. et al. *DNA* 7(10): 671–77 (1988).
Rickles, R. J. et al., *J. Biol. Chem.* 263(3): 1563–69 (1988).
Bennett, W. F. et al., *Fibrinolysis* 4 (Supplement 3): 14 (1990) Abstract No. 37.
Paoni, N. F. et al., *Fibrinolysis* 4 (Supplement 3): 90 (1990) Abstract No. 228.
Keyt, B. et al., *Fibrinolysis* 4 (Supplement 3): 164 (1990) Abstract No. 423.

*Primary Examiner*—Robert J. Hill, Jr.
*Assistant Examiner*—Marianne Porta Allen
*Attorney, Agent, or Firm*—Ginger R. Dreger

[57] ABSTRACT

Biologically active tissue plasminogen activator (t-PA) variants with decreased clearance as compared to wild-type t-PA are prepared, including variants that have one or more amino acid alterations in at least the kringle-1 and/or kringle-2 domain(s) of the molecule. DNA sequences can be prepared that encode the variants, as well as expression vectors incorporating the DNA sequences and host cells transformed with the expression vectors. The variants may be used in pharmaceutical preparations to treat a vascular disease or condition, or to prevent fibrin deposition or adhesion formation or reformation in mammals.

17 Claims, 3 Drawing Sheets

TISSUE PLASMINOGEN ACTIVATOR VARIANTS WITH DECREASED CLEARANCE

This is a continuation of application Ser. No. 07/912,040 filed on Jul. 09, 1992 now U.S. Pat. No. 5,246,850 issued Sep. 21, 1993, which is a continuation of application Ser. No. 07/560,515 filed Jul. 31, 1990, now abandoned.

BACKGROUND OF THE INVENTION

I. Field of the Invention

This invention is directed to particular tissue plasminogen activator (t-PA) variants, to methods for preparing these variants, and to methods and compositions utilizing the variants in pharmaceutical compositions. Specifically, this invention relates to t-PA variants with modified amino acid sequences, including substitutions, within at least the kringle-1 or kringle-2 domains of t-PA that result in the variants having a decreased rate of clearance as compared to wild-type t-PA.

II. Description of Background and Related Art

Plasminogen activators are enzymes that cleave the peptide bond of plasminogen between amino acid residues 561 and 562, converting it to plasmin. Plasmin is an active serine proteinase that degrades various proteins including fibrin. Several plasminogen activators have been identified including streptokinase (a bacterial protein), urokinase (synthesized in the kidney and elsewhere and originally extracted from urine), and human tissue plasminogen activator, termed t-PA (produced by the cells lining blood vessel walls).

The mode of action of each of these plasminogen activators is somewhat different. Streptokinase forms a complex with plasminogen or plasmin generating plasminogen-activating activity, urokinase cleaves plasminogen directly, and t-PA interacts with both plasminogen and fibrin for optimal activity.

Due in part to its high fibrin specificity and potent ability to dissolve blood clots in vivo, t-PA has been identified as an important new biological pharmaceutical for treating vascular diseases such as myocardial infarction.

A substantially pure form of t-PA was first produced from a natural source and tested for in vivo activity by Collen et al., U.S. Pat. No. 4,752,603 issued 21 June 1988 (see also Rijken et al., J, Biol. Chem., 256:7035 [1981]). Pennica et al. (Nature, 301:214 [1983]) determined the DNA sequence of t-PA and deduced the amino acid sequence from this DNA sequence (see U.S. Pat. No. 4,766,075 issued Aug. 23, 1988).

Human native t-PA has potential N-linked glycosylation sites at amino acid positions 117, 184, 218, and 448. A high mannose oligosaccharide is present at position 117 and a complex oligosaccharide is present at positions 184 and 448. Sites 117 and 448 appear to always be glycosylated, while site 184 is thought to be glycosylated in about fifty percent of the molecules. The partial glycosylation pattern at position 184 may be due to site 184 being situated in an unexposed region of the molecule. The t-PA molecules that are glycosylated at position 184 are termed Type I t-PA, and the molecules that are not glycosylated at position 184 are termed Type II t-PA. Position 218 has not been found to be glycosylated in native t-PA.

Research on the structure of t-PA has identified the molecule as having five domains. Each domain has been defined with reference to homologous structural or functional regions in other proteins such as trypsin, chymotrypsin, plasminogen, prothrombin, fibronectin, and epidermal growth factor (EGF). These domains have been designated, starting at the N-terminus of the amino acid sequence of t-PA, as the finger (F) domain from amino acids 1 to about 44, the growth factor (G) domain from about amino acids 45 to 91 (based on homology with EGF), the kringle-1 (K1) domain from about amino acids 92–173, the kringle-2 (K2) domain from about amino acids 180 to 261, and the serine protease (P) domain from about amino acid 264 to the carboxyl terminus at amino acid 527. These domains are situated essentially adjacent to each other, and some are connected by short "linker" regions. These linker regions bring the total number of amino acids of the mature polypeptide to 527, although three additional residues (Gly-Ala-Arg) may be found at the amino terminus and are probably the result of incomplete precursor processing of the molecule.

Each domain is believed to confer certain biologically significant properties on the t-PA molecule. The finger domain is thought to be important in the high binding affinity of t-PA to fibrin. This activity appears to be important for the high specificity that t-PA displays with respect to clot lysis at the locus of a fibrin-rich thrombus. The kringle-1 and kringle-2 domains also appear to be associated with fibrin binding and with the ability of fibrin to stimulate the activity of t-PA. The serine protease domain is responsible for the enzymatic activity of t-PA which results in the conversion of plasminogen to plasmin. The t-PA molecule is often cleaved between position 275 and position 276 (located in this serine protease domain) to generate the 2-chain form of the molecule.

Natural t-PA has a plasma half-life of about six minutes or less when administered to patients in therapeutically effective amounts. In certain situations, a six-minute half-life is desirable, as for example, in aggressive therapy of a life-threatening disease such as myocardial infarction or pulmonary embolism. In these high-risk situations, patients who have significant or unrecognized potential for uncontrolled bleeding may be treated with t-PA. If such bleeding occurs, drug administration can be stopped and the causative t-PA levels will rapidly drop. Thus, treatment of these patients with a relatively short-lived form of t-PA is preferred.

Despite the profound advantages associated with natural t-PA as a clot-dissolving agent, it is not believed that the naturally occurring form of the protein necessarily represents the optimal t-PA agent under all circumstances. In some instances, such as treatment of deep vein thrombosis, treatment following reperfusion of an infarct victim, treatment of pulmonary embolism, or treatment using bolus injection, a t-PA molecule with a longer half-life and/or decreased clearance is desirable. Several variants of the wild-type t-PA molecule have been generated in attempts to increase half-life or decrease the clearance rate.

One method used to generate such t-PA variants has been to delete individual amino acids, partial domains, or complete domains from the molecule. For example, removal of part or all of the finger domain of t-PA as described in U.S. Pat. No. 4,935,237 (issued Jun. 19, 1990) results in a molecule with decreased clearance, although it has substantially diminished fibrin-binding characteristics. Browne et al. (J. Biol. Chem., 263:1599 [1988]) deleted the region between amino acids 57 and 81 and found the resulting variant to have a slower clearance from plasma. Collen et al. (*Blood*, 71:216 [1988]) deleted amino acids 6–86 (part of the finger and growth domains) and found that this mutant had a half-life in rabbits of 15 minutes as compared with 5 minutes for wild-type t-PA. Similarly, Kaylan et al. (*J. Biol. Chem.*, 263:3971 [1988]) deleted amino acids 1–89 and found that the half-life of this mutant in mice was about fifteen minutes as compared to about two minutes for wild-type t-PA. Cambier et al. (*J. Cardiovasc. Pharmacol.*, 11:468 [1988]) constructed a variant with the finger and growth factor domains deleted and the three asparagine glycosylation sites abolished. This variant was shown to have a longer half-life than wild-type t-PA when tested in dogs. Variants with only the growth factor domain or the finger domain deleted have also been demonstrated to have decreased clearance rates in rabbits, guinea pigs and rats (Higgins and Bennett, *Ann. Rev. Pharmacol. Toxicol.*, 30:91 [1990] and references therein).

Various deletions in the growth factor region have also been reported in the patent literature. See EPO Publication Number 241,208 (deletion of amino acids 51–87, and deletion of amino acids 51–173). See also EPO Publication Number 240,334 which describes the modification of mature, native t-PA in the region of amino acids 67-69 by deletion or substitution of one or more amino acids.

Another means to improve the clearance rate and/or half-life of t-PA has been to complex the t-PA molecule with a second molecule. For example, a t-PA-polyethylene-glycol conjugate has been reported to enhance the rate of clearance of t-PA, as reported in EPO 304,311 (published Feb. 22, 1989). A monoclonal antibody to t-PA has been reported to increase the functional half-life of t-PA in vivo without decreasing its activity (see EPO 339,505 published Nov. 2, 1989).

A variety of amino acid substitution t-PA variants have been evaluated for their ability to decrease the clearance rate or increase the half-life of t-PA. The variant R275E (where arginine at position 275 of native, mature t-PA was substituted with glutamic acid) has been shown to have a clearance rate of about two times slower than that of wild-type t-PA when tested in primates and rabbits (Hotchkiss et al., *Thromb. Haemost.*, 58:491 [1987]). Substitutions in the region of amino acids 63–72 of mature, native t-PA, and especially at positions 67 and 68, have been reported to increase the plasma half-life of t-PA (see WO 89/12681, published Dec. 28, 1989).

Production of other substitution variants has focused on converting the glycosylation sites of t-PA to nonglycosylated sites. Hotchkiss et al. (*Thromb. Haemost*, 60:255 [1988]) selectively removed oligosaccharide residues from the t-PA molecule, and demonstrated that the removal of these residues decreased the rate of clearance of t-PA when tested in rabbits. Removal of the high mannose oligosaccharide at position 117 using the enzyme endo-$\beta$-N-acetylglucosaminidase H (Endo-H) resulted in a rate of clearance that was decreased about two fold. Oxidation of nearly all oligosaccharide residues using sodium periodate resulted in a rate of clearance nearly three fold lower than wild-type t-PA. These researchers also generated the t-PA variant N117Q (wherein asparagine at position 117 of native, mature t-PA was substituted with glutamine) to prevent glycosylation at position 117. The clearance rate of this variant was lower than wild-type t-PA. See also EP 238,304 published Sep. 23, 1987 and EP 227,462 published Jul. 1, 1987.

An additional approach to produce t-PA variants with extended circulatory half-life -and slower clearance has been to add glycosylation sites to the molecule. As examples of this approach, positions 60, 64, 65, 66, 67, 78, 79, 80, 81, 82, and 103 have been substituted with appropriate amino acids to create molecules with glycosylation sites at or near some of these residues (see WO 89/11531, published 30 November 1989 and U.S. Ser. No. 7/480691, filed Feb. 15, 1990) now abandoned.

While some of the above cited work has resulted in generation of t-PA variants with increased half-life or decreased clearance rates, in many instances the activity, solubility, and/or fibrin-binding specificity of the molecule has been compromised. Thus, the known t-PA variants have not possessed optimal characteristics.

Accordingly, it is an object of this invention to prepare t-PA variants with decreased clearance rates that substantially retain biological activity, solubility and/or fibrin specificity. Production of t-PA variants with decreased clearance that possess any one or a combination of these characteristics will improve the therapeutic value and efficacy of t-PA. A further object of this invention is to produce t-PA variants with improved efficacy or pharmaceutical utility.

SUMMARY OF THE INVENTION

In accordance with the objects of this invention, t-PA variants are provided that exhibit biological activity and have decreased clearance rates as compared to wild-type t-PA.

More specifically, the invention provides a t-PA amino acid sequence variant with an alteration at position 94 or 95, or at positions 236, 238, and 240, that exhibits biological activity and has a decreased clearance as compared to wild-type t-PA.

In another preferred embodiment, the alteration at positions 94 or 95, or at positions 236, 238 and 240 is a substitution, and the substituted amino acids are replaced with preferably alanine, glycine, serine or threonine. In a most preferred embodiment, they are replaced with alanine, or in certain positions, glycine.

In other embodiments, the t-PA variants are altered at more than one position such as at positions 94 and 95, or at positions 94, 236, 238 and 240, or at positions 95, 236, 238, and 240, or at positions 94, 95, 236, 238, and 240. Preferably, the alteration will be an amino acid substitution, preferably with alanine, glycine, serine, or threonine, and most preferably with alanine, or at certain positions, glycine.

In another embodiment, the above described t-PA variants, substituted at positions 94 or 95 or both, or at positions 236, 238, and 240, or at positions 94, 236, 238 and 240, or at positions 95, 236, 238, and 240, or at positions 94, 95, 236, 238, and 240 are additionally altered at position 103 and/or position 117 and the alteration is preferably an amino acid substitution with asparagine at position 103 and alanine or serine, or preferably glutamine, at position 117.

In other embodiments, the invention relates to a DNA sequence encoding the variants described above, replicable expression vectors capable of expressing this DNA sequence in a transformed host cell, and transformed host cells.

In yet another embodiment, the invention relates to a composition for treating a vascular condition or disease comprising a therapeutically effective amount of the t-PA variant in admixture with a pharmaceutically acceptable carrier.

In still another embodiment, the invention provides a method of treating a vascular disease or condition in a mammal comprising administering an effective amount of the t-PA variant to the mammal.

In still another embodiment, the invention provides a composition for preventing fibrin deposition or adhesion formation or reformation comprising a therapeutically effective amount of the t-PA variant in admixture with a pharmaceutically acceptable carrier.

In one other embodiment, the invention is directed to a method for treating a mammal to prevent fibrin deposition or adhesion formation or reformation comprising administering to a site on the mammal of potential fibrin or adhesion formation an effective amount of the t-PA variant.

DETAILED DESCRIPTION OF THE INVENTION

I. Definitions

The terms "t-PA" "human t-PA" and "human tissue plasminogen activator" refer to human extrinsic (tissue-type) plasminogen activator having two functional regions consisting of a protease domain that is capable of converting plasminogen to plasmin and an N-terminal region believed to be responsible for fibrin binding. These terms thus include polypeptides containing these functional domains as part of the amino acid sequence of the polypeptide. Biologically active forms of t-PA may be produced by recombinant cell culture systems in forms comprising the two functional regions of the molecule and any other portions of t-PA otherwise native to the source of the t-PA. It will be understood that natural allelic variations exist and can occur among individuals, as demonstrated by one or more amino acid differences in the amino acid sequence of t-PA of each individual.

The terms "wild-type t-PA" and "native t-PA" refer to native-sequence human t-PA, i.e., that encoded by the cDNA sequence reported in U.S. Pat. No. 4,766,075, issued Aug. 23, 1988, the disclosure of which is incorporated by reference. Amino acid site numbers or positions in the t-PA molecule are labelled in accordance with U.S. Pat. No. 4,766,075, supra. The t-PA may be from any native source and includes the corresponding proteins of various animals such as humans. In addition, the t-PA may be obtained from any recombinant expression system, including, for example, Chinese hamster ovary (CHO cells) or human embryonic kidney 293 cells.

The terms "amino acid" and "amino acids" refer to all naturally occurring L-α-amino acids. This definition is meant to include norleucine, ornithine, and homocysteine. The amino acids are identified by either the single-letter or three-letter designations:

Asp D aspartic acid
Ile I isoleucine
Thr T threonine
Leu L leucine
Ser S serine
Tyr Y tyrosine
Glu E glutamic acid
Phe F phenylalanine
Pro P proline
His H histidine
Gly G glycine
Lys K lysine
Ala A alanine
Arg R arginine
C cysteine
Trp W tryptophan
Val V valine
Gln Q glutamine
Met M methionine
Asn N asparagine These amino acids may be classified according to the chemical composition and properties of their side chains. They are broadly classified into two groups, charged and uncharged. Each of these groups is divided into subgroups to classify the amino acids more accurately:

I. Charged Amino Acids
  Acidic Residues: aspartic acid, glutamic acid
  Basic Residues: lysine, arginine, histidine
II. Uncharged Amino Acids
  Hydrophilic Residues: serine, threonine, asparagine, glutamine
  Aliphatic Residues: glycine, alanine, valine, leucine, isoleucine
  Non-polar Residues: cysteine, methionine, proline
  Aromatic Residues: phenylalanine, tyrosine, tryptophan The terms "alteration" "amino acid sequence alteration" "variant" and "amino acid sequence variant" refer to t-PA molecules with some differences in their amino acid sequences as compared to native t-PA. Ordinarily, the variants will possess at least 80% homology with native t-PA, and preferably, they will be at least about 90% homologous with native t-PA. The amino acid sequence variants of t-PA falling within this invention possess substitutions, deletions, and/or insertions at certain positions. These positions have been identified by the inventors to be influential in modulating the clearance rate of t-PA.

Substitutional t-PA variants are those that have at least one amino acid residue in the native t-PA sequence removed and a different amino acid inserted in its place at the same position. The substitutions may be single, where only one amino acid in the molecule has been substituted, or they may be multiple, where two or more amino acids have been substituted in the same molecule.

Substantial changes in the activity of the t-PA molecule may be obtained by substituting an amino acid with a side chain that is significantly different in charge and/or structure from that of the native amino acid. This type of substitution would be expected to affect the structure of the polypeptide backbone and/or the charge or hydrophobicity of the molecule in the area of the substitution.

Moderate changes in the activity of the t-PA molecule would be expected by substituting an amino acid with a side chain that is similar in charge and/or structure to that of the native molecule. This type of substitution, referred to as a conservative substitution, would not be expected to substantially alter either the structure of the polypeptide backbone or the charge or hydrophobicity of the molecule in the area of the substitution.

Insertional t-PA variants are those with one or more amino acids inserted immediately adjacent to an amino acid at a particular position in the native t-PA molecule. Immediately adjacent to an amino acid means connected to either the α-carboxy or α-amino functional group of the amino acid. The insertion may be one or more amino acids. Ordinarily, the insertion will consist of one or two conservative amino acids. Amino acids similar in charge and/or structure to the amino acids adjacent to the site of insertion are defined as conservative. Alternatively, this invention includes insertion of an amino acid with a charge and/or structure that is substantially different from the amino acids adjacent to the site of insertion.

Deletional variants are those with one or more amino acids in the native t-PA molecule removed. Ordinarily, deletional variants will have one or two amino acids deleted in a particular region of the t-PA molecule.

The notations used throughout this application to describe t-PA amino acid sequence variants are described below. The location of a particular amino acid in the polypeptide chain of t-PA is identified by a number. The number refers to the amino acid position in the amino acid sequence of the mature, wild-type human t-PA polypeptide as disclosed in U.S. Pat. No. 4,766,075, issued Aug. 23, 1988. In the present application, similarly positioned residues in t-PA variants are designated by these numbers even though the actual residue number is not so numbered due to deletions or insertions in the molecule. This will occur, for example, with site-directed deletional or insertional variants. The amino acids are identified using the one-letter code. Substituted amino acids are designated by identifying the wild-type amino acid on the left side of the number denoting the position in the polypeptide chain of that amino acid, and identifying the substituted amino acid on the right side of the number.

For example, replacing the amino acid glutamic acid (E) at position 94 of t-PA with alanine (A) is designated as E94A. Replacing glutamic acid (E) at position 94 with alanine and aspartic acid (D) at position 95 with alanine would be indicated as E94A,D95A. Deletional variants are identified by indicating the amino acid residue and position at either end of the deletion, inclusive, and placing the Greek letter delta "Δ" to the left of the indicated amino acids. For example, a t-PA variant containing a deletion of amino acids 100-101 would be indicated as ΔY100-R101, where Y and R indicate the amino acids tyrosine and arginine, respectively. Deletion of a single amino acid, for example Y100, would be indicated as ΔY100. Insertional t-PA variants are designated by the use of brackets "[]" around the inserted amino acids, and the location of the insertion is denoted by indicating the position of the amino acid on either side of the insertion. For example, an insertion of the amino acids alanine (A) and valine (V) between glutamic acid at position 94 and aspartic acid at position 95 is indicated as E94[A,V]D95. For ease of reading, a comma "," is used to separate multiple mutations that occur in a single molecule, and a semi-colon ";" is used to separate individual t-PA variant molecules that have been constructed, where several t-PA variant molecules are listed together.

The terms "clearance rate" and "clearance" refer to rate at which the t-PA molecule is removed from the bloodstream. Clearance is measured with respect to native t-PA, such that decreased clearance indicates that the t-PA variant is cleared more slowly than native t-PA, and increased clearance indicates that the t-PA variant is cleared more rapidly than native t-PA.

The terms "biological activity" "biologically active" "activity" and "active" refer to the ability of the t-PA molecule to convert plasminogen to plasmin as measured in the S-2251 assay in the presence of a plasma clot or in the presence of fibrin, the S-2288 assay, the plasma clot lysis assay, or other appropriate assays. The t-PA molecule may be assayed in its one or two chain form, and the assay(s) may be conducted in the presence or absence of potential modulators of activity such as fibrin, fibrinogen, plasma and/or plasma clots.

The terms "DNA sequence encoding" "DNA encoding" and "nucleic acid encoding" refer to the order or sequence of deoxyribonucleotides along a strand of deoxyribonucleic acid. The order of these deoxyribonucleotides determines the order of amino acids along the polypeptide chain. The DNA sequence thus codes for the amino acid sequence..

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host cell. The vector is used to transport the foreign or heterologous DNA into a suitable host cell. Once in the host cell, the vector can replicate independently of the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

The terms "transformed host cell" and "transformed" refer to the introduction of DNA into a cell. The cell is termed a "host cell" and it may be a prokaryotic or a eukaryotic cell Typical prokaryotic host cells include various strains of *E. coli*. Typical eukaryotic host cells are mammalian, such as Chinese hamster ovary cells or human embryonic kidney 293 cells. The introduced DNA is usually in the form of a vector containing an inserted piece of DNA. The introduced DNA sequence may be from the same species as the host cell or a different species from the host cell, or it may be a hybrid DNA sequence, containing some foreign and some homologous DNA.

II. GENERAL METHODS

A. Selection Of Variants

The clearance rate of t-PA can be modulated by altering the amino acid sequence of the molecule. The alterations may be insertions, deletions and/or substitutions of amino acids. Preferably, the alterations will be by substitution of at least one amino acid in one or more regions of the molecule. A suitable technique for selecting the amino acid(s) to be substituted is that of alanine-scanning mutagenesis, as described by Cunningham and Wells (*Science,* 244:1081 [1989]). In this technique, one or more amino acids with charged side-chains are replaced by amino acids with uncharged side-chains. Such changes are believed to affect the interaction of the polypeptide with the surrounding aqueous environment.

For alanine-scanning mutagenesis, the amino acids for use in substitution are those that will neutralize the charge of the corresponding amino acid of wild-type t-PA. Any hydrophobic, aliphatic, aromatic, or nonpolar amino acid can be used. Among these, amino acids with small side-chains such as alanine, serine and threonine are preferred to those with larger side chains such as valine, leucine, and isoleucine. Preferably, the amino acid used for replacement is either glycine, alanine, serine, threonine, glutamine, or asparagine. Most preferably, the amino acid used for replacement is alanine, or, at certain positions, asparagine, glycine or glutamine. Alanine is the most preferred amino acid for this purpose because it eliminates the side-chain beyond the beta-carbon, and is thus less likely to alter the tertiary conformation of wild-type t-PA. Further, alanine is frequently found in both buried and exposed regions of proteins (Chothia, *J. Mol. Biol.,* 150:1 [1976]).

Exemplary variants with decreased clearance and/or increased half-life will have at least one alteration (amino acid substitution, deletion and/or insertion) of the wild-type t-PA amino acid sequence in either the kringle-1 domain or the kringle-2 domain. The variants may also contain additional alterations of residues in other domains of the wild-type sequence that further enhance the properties of the molecule. For example, these additional alterations may serve to increase fibrin-binding specificity, specific activity, and/or zymogenicity of the t-PA variant.

In one preferred embodiment, the amino acid at position 94 or 95, or the amino acids at positions 236, 238, and 240, or combinations of these positions will be substituted, preferably with alanine, or glycine. Each of these molecules may also contain other amino acid substitutions, deletions or insertions, preferably a substitution of asparagine for threonine at position 103 (see WO 89/11531 published Nov. 30, 1989 and U.S. Ser. No. 07/480691 filed Feb. 15, 1990) and/or a substitution of alanine or serine, or preferably glutamine, for asparagine at position 117. Representative t-PA variants of this invention include E94A; D95A; D95G; E94A,D-95A; D236A,D238A,K240A; E94A,D95A,N117Q; E9-4A,D95A,D236A,D238A,K240A; T103N,D236A,D2-38A,K240A; and N117Q, D236A, D238A, K240A.

In addition, the molecules of this invention may be substituted or deleted at certain positions to confer additional desired properties including increased fibrin specificity or zymogenicity. These positions include, for example, deletion of amino acids 92 to 179, deletions in the region of amino acids 174– 261, modification at glycosylation sites such as position 184 and/or modifications in the region of amino acids 244–255. Other key positions for modification are located throughout the protease domain and include, for example, position 275 (see EPO 233,013 published Aug. 19, 1987 and WO 87/04722, published Aug. 13, 1987), position 277 (see EPO 297,066, published Dec. 28, 1988 and EPO 201,153 published Nov. 12, 1986) and positions 296–299 as disclosed in WO 90/02798 published Mar. 22, 1990.

B. Construction Of Variants

The t-PA amino acid sequence variants of this invention are preferably constructed by mutating the DNA sequence that encodes wild-type t-PA. Generally, particular regions or sites of the DNA will be targeted for mutagenesis, and thus the general methodology employed to accomplish this is termed site-directed mutagenesis. The mutations are made using DNA modifying enzymes such as restriction endonucleases (which cleave DNA at particular locations), nucleases (which degrade DNA) and/or polymerases (which synthesize DNA).

1. Deletions and Insertions

Restriction endonuclease digestion of DNA followed by ligation may be used to generate deletions, as described in section 15.3 of Sambrook et al. (*Molecular Cloning: A Laboratory Manual,* second edition, Cold Spring Harbor Laboratory Press, New York [1989]). To use this method, it is preferable that the foreign DNA be inserted into a plasmid vector. A restriction map of both the foreign (inserted) DNA and the vector DNA must be available, or the sequence of the foreign DNA and the vector DNA must be known. The foreign DNA must have unique restriction sites that are not present in the vector. Deletions are then made in the foreign DNA by digesting it between these unique restriction sites, using the appropriate restriction endonucleases under conditions suggested by the manufacturer of the enzymes. If the restriction enzymes used create blunt ends or compatible ends, the ends can be directly ligated together using a ligase such as bacteriophage T4 DNA ligase and incubating the mixture at 16° C. for 1–4 hours in the presence of ATP and ligase buffer as described in section 1.68 of Sambrook et al., supra. If the ends are not compatible, they must first be made blunt by using the Klenow fragment of DNA polymerase I or bacteriophage T4 DNA polymerase, both of which require the four deoxyribonucleotide triphosphates to fill-in the overhanging single-stranded ends of the digested DNA. Alternatively, the ends may be blunted using a nuclease such as nuclease S1 or mung-bean nuclease, both of which function by cutting back the overhanging single strands of DNA. The DNA is then religated using a ligase. The resulting molecule is a t-PA deletion variant.

A similar strategy may be used to construct insertion variants, as described in section 15.3 of Sambrook et al., supra. After digestion of the foreign DNA at the unique restriction site(s), an oligonucleotide is ligated into the site where the foreign DNA has been cut. The oligonucleotide is designed to code for the desired amino acids to be inserted and additionally has 5' and 3' ends that are compatible with the ends of the foreign DNA that have been digested, such that direct ligation is possible.

2. Oligonucleotide-Mediated Mutagenesis

Oligonucleotide-directed mutagenesis is the preferred method for preparing the substitution variants of this invention. It may also be used to conveniently prepare the deletion and insertion variants of this invention. This technique is well known in the art as described by Adelman et al. (*DNA,* 2:183 [1983]).

Generally, oligonucleotides of at least 25 nucleotides in length are used to insert, delete or substitute two or more nucleotides in the t-PA molecule. An optimal oligonucleotide will have 12 to 15 perfectly matched nucleotides on either side of the nucleotides coding for the mutation. This ensures that the oligonucleotide will hybridize properly to the single-stranded DNA template molecule. The oligonucleotides are readily synthesized using techniques well known in the art such as that described by Crea et al. (*Proc. Nat'l. Acad. Sci. USA*, 75:5765 [1978]), specifically incorporated by reference.

The DNA template molecule is the single-stranded form of the vector with its wild-type cDNA t-PA insert. The single-stranded template can only be generated by those vectors that are either derived from bacteriophage M13 vectors (the commercially available M13mp18 and M13mp19 vectors are suitable), or those vectors that contain a single-stranded phage origin of replication as described by Veira et al. (*Meth. Enzymol.*, 153:3 [1987]). Thus, the cDNA t-PA that is to be mutated must be inserted into one of these vectors in order to generate single-stranded template. Production of the single-stranded template is described in sections 4.21–4.41 of Sambrook et al., supra.

To mutagenize the wild-type t-PA, the oligonucleotide is annealed to the single-stranded DNA template molecule under suitable hybridization conditions. A DNA polymerizing enzyme, usually the Klenow fragment of *E. coli* DNA polymerase I, is then added. This enzyme uses the oligonucleotide as a primer to complete the synthesis of the mutation-bearing strand of DNA. Thus, a heteroduplex molecule is formed such that one strand of DNA encodes the wild-type t-PA inserted in the vector, and the second strand of DNA encodes the mutated form of t-PA inserted into the same vector. This heteroduplex molecule is then transformed into a suitable host cell, usually a prokaryote such as *E. coli* JM101. After growing the cells, they are plated on to agarose plates and screened using the oligonucleotide primer radiolabeled with 32-P to identify the colonies that contain the mutated t-PA. These colonies are selected, and the DNA is sequenced to confirm the presence of mutations in the t-PA molecule.

Mutants with more than one amino acid substituted may be generated in one of several ways. If the amino acids are located close together in the polypeptide chain, they may be mutated simultaneously using one oligonucleotide that codes for all of the desired amino acid substitutions. If however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant. The first round is as described for the single mutants: wild-type t-PA DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

To express the DNA encoding the t-PA variant as a polypeptide, this DNA is excised from the vector and inserted into an expression vector that is appropriate for eukaryotic host cell expression. Chinese hamster ovary (CHO) cells are preferred for long-term stable t-PA production. However, this invention is not limited to expression of t-PA variants in Clio cells, as it is known that numerous other cell types can be used, particularly if only transient expression of the t-PA variants is necessary, as for experimental purposes.

C. Host Cell Cultures And Vectors

1. Prokaryotic Cells

Prokaryotes are the preferred host cells for the initial cloning steps of this invention. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include *E. coli* K12 strain 294 (ATCC number 31,446), *E. coli* strain W3110 (ATCC number 27,325) *E. coli* X1776 (ATCC number 31,537), and *E. coli* B; however many other strains of *E. coli*, such as HB101, JM101, NM522, NM53B, NM539, and many other species and genera of prokaryotes may be used as well.

Prokaryotes may also be used as hosts for expression of DNA sequences. The *E. Coli* strains listed above, bacilli such as *Bacillus subtilis*, other enterobacteriaceae such as *Salmonella typhimurium* or *Serratia marcesans*, and various *Pseudomonas* species may all be used as hosts.

Plasmid vectors containing replicon and control sequences that are derived from species compatible with the host cell are used with these hosts. The vector usually has a replication site, marker genes that provide phenotypic selection in transformed cells, one or more promoters, and a polylinker region containing several restriction sites for insertion of foreign DNA. Plasmids typically used for transformation of *E. coli* include pBR322, pUC18, pUC19, pUC118, pUC119, and Bluescript M13, all of which are described in sections 1.12–1.20 of Sambrook et al., supra. However, many other suitable vectors are available as well. These vectors contain genes coding for ampicillin and/or tetracycline resistance which enables cells transformed with these vectors to grow in the presence of these antibiotics.

The promoters most commonly used in prokaryotic vectors include the β-lactamase (penicillinase) and lactose promoter systems (Chang et al. *Nature*, 375:615 [1978]; Itakura et al., *Science*, 198:1056 [1977]; Goeddel et al., *Nature*, 281:544 [1979]) and a tryptophan (trp) promoter system (Goeddel et al., *Nucl. Acids Res.*, 8:4057 [1980]; EPO Appl. Publ. No. 36,776), and the alkaline phosphatase systems. While these are the most commonly used, other microbial promoters have been utilized, and details concerning their nucleotide sequences have been published, enabling a skilled worker to ligate them functionally into plasmid vectors (see Siebenlist et al., *Cell*, 20:269 [1980]).

2. Eukaryotic Microbes

Eukaryotic microbes such as yeasts may be used to practice this invention. The baker's yeast Saccharomyces cerevisiae, is a commonly used eukaryotic microorganism, although several other strains are available. The plasmid YRp7 (Stinchcomb et al., *Nature*, 282:39 [1979]; Kingsman et al., *Gene*, 7:141 [1979]; Tschemper et al., *Gene*, 10:157 [1980]) is commonly used as an expression vector in *Saccharomyces*. This plasmid contains the trp 1 gene that provides a selection marker for a mutant strain of yeast lacking the ability to grow in tryptophan, such as strains ATCC No. 44,076 and PEP4-1 (Jones, *Genetics*, 85:12 [1977]). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., *J. Biol. Chem.*, 255:2073 [1980]) or other glycolytic enzymes (Hess et al., *J. Adv. Enzyme Reg.*, 7:149 [1968]; Holland et al., *Biochemistry*, 17:4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In the construction of suitable expression plasmids, the termination sequences associated with these genes are also ligated into the expression vector 3′of the sequence desired to be expressed to provide polyadenylation of the mRNA and termination. Other promoters that have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

3. Eukaryotic Multicellular Organisms

Cell cultures derived from multicellular organisms may be used as hosts to practice this invention. While both invertebrate and vertebrate cell cultures are acceptable, vertebrate cell cultures, particularly mammalian cultures, are preferable. Examples of suitable cell lines include monkey kidney CVI line transformed by SV40 (COS-7, ATCC CRL 1651); human embryonic kidney line 293S (Graham et al., *J. Gen. Virol.*, 36:59 [1977]); baby hamster kidney cells (BHK, ATCC COL 10); Chinese hamster ovary cells (Urlab and Chasin, *Proc. Natl. Acad. Sci USA*, 77:4216 [1980]); mouse sertoli cells (TM4, Mather, *Biol. Repro.*, 23:243 [1980]); monkey kidney cells (CVI-76, ATCC COL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL 51); rat hepatoma cells (HTC, MI.54, Baumann et al., *J. Cell Biol.*, 85:1 [1980]); and TRI cells (Mather et al., *Annals N.Y. Acad. Sci.*, 383:44 [1982]). Expression vectors for these cells ordinarily include (if necessary) DNA sequences for an origin of replication, a promoter located in front of the gene to be expressed, a ribosome binding site, an RNA splice site, a polyadenylation site, and a transcription terminator site.

Promoters used in mammalian expression vectors are often of vital origin. These vital promoters are commonly derived from polyoma virus, Adenovirus2, and most frequently Simian Virus 40 (SV40). The SV40 virus contains two promoters that are termed the early and late promoters. These promoters are particularly useful because they are both easily obtained from the virus as one DNA fragment that also contains the viral origin of replication (Fiers et al., *Nature*, 273:113 [1978]). Smaller or larger SV40 DNA fragments may also used, provided they contain the approximately 250-bp sequence extending from the HindIII site toward the BgII site located in the vital origin of replication.

Alternatively, promoters that are naturally associated with the foreign gene (homologous promoters) may be used provided that they are compatible with the host cell line selected for transformation.

An origin of replication may be obtained from an exogenous source, such as SV40 or other virus (e.g., Polyoma, Adeno, VSV, BPV) and inserted into the cloning vector. Alternatively, the origin of replication may be provided by the host cell chromosomal replication mechanism. If the vector containing the foreign gene is integrated into the host cell chromosome, the latter is often sufficient.

Satisfactory amounts of human t-PA are produced by transformed cell cultures. However, the use of a secondary DNA coding sequence can enhance production levels. The secondary coding sequence typically comprises the enzyme dihydrofolate reductase (DHFR). The wild-type form of DHFR is normally inhibited by the chemical methotrexate (MTX). The level of DHFR expression in a cell will vary depending on the amount of MTX added to the cultured host cells. An additional feature of DHFR that makes it particularly useful as a secondary sequence is that it can be used as a selection marker to identify transformed cells.

Two forms of DHFR are available for use as secondary sequences, wild-type DHFR and MTX-resistant DHFR. The type of DHFR used in a particular host cell depends on whether the host cell is DHFR deficient (such that it either produces very low levels of DHFR endogenously, or it does not produce functional DHFR at all). DHFR-deficient cell lines such as the CHO cell line described by Urlaub and Chasin (*Proc. Natl. Acad. Sci.* (USA) 72:4216 [1980]) are transformed with wild-type DHFR coding sequences. After transformation, these DHFR-deficient cell lines express functional DHFR and are capable of growing in a culture medium lacking the nutrients hypoxanthine, glycine and thymidine. Nontransformed cells will not survive in this medium.

The MTX-resistant form of DHFR can be used as a means of selecting for transformed host cells in those host cells that endogenously produce normal amounts of functional DHFR that is MTX sensitive. The CHO-K1 cell line (ATCC number CL 61) possesses these characteristics, and is thus a useful cell line for this purpose. The addition of MTX to the cell culture medium will permit only those cells transformed with the DNA encoding the MTX-resistant DHFR to grow. The nontransformed cells will be unable to survive in this medium.

4. Secretion Systems

Many eukaryotic proteins normally secreted from the cell contain an endogenous signal sequence as part of the amino acid sequence. This sequence targets the protein for export from the cell via the endolasmic reticulum and Golgi apparatus. The signal sequence is typically located at the amino terminus of the protein, and ranges in length from about 13 to about 36 amino acids. Although the actual sequence varies among proteins, all known eukaryotic signal sequences contain at least one positively charged residue and a highly hydrophobic stretch of 10-15 amino acids (usually rich in the amino acids luecine, isoleucine, alanine, valine and phenylalanine) near the center of the signal sequence. The signal sequence is normally absent from the secreted form of the protein, as it is cleaved by a signal peptidase located on the endoplasmic reticulum during translocation of the protein into the endoplasmic reticulum. The protein with its signal sequence still attached is often referred to as the 'pre-protein' or the immature form of the protein.

However, not all secreted proteins contain an amino terminal signal sequence that is cleaved. Some proteins, such as ovalbumin, contain a signal sequence that is located on an internal region of the protein. This sequence is not normally cleaved during translocation.

Proteins normally found in the cytoplasm can be targeted for secretion by linking a signal sequence to the protein. This is readily accomplished by ligating DNA encoding a signal sequence to the 5' end of the DNA encoding the protein and then expressing this fusion protein in an appropriate host cell. The DNA encoding the signal sequence may be obtained as a restriction fragment from any gene encoding a protein with a signal sequence. Thus, prokaryotic, yeast, and eukaryotic signal sequences may be used herein, depending on the type of host cell utilized to practice the invention. The DNA encoding the signal sequence portion of the gene is excised using appropriate restriction endonucleases and then ligated to the DNA encoding the protein to be secreted, i.e. t-PA.

Selection of a functional signal sequence requires that the signal sequence is recognized by the host cell signal peptidase such that cleavage of that signal sequence and secretion of the protein will occur. The DNA and amino acid sequence encoding the signal sequence portion of several eukaryotic genes including, for example, human growth hormone, proinsulin, and proalbumin are known (see Stryer, *Biochemistry*, W.H. Freeman and Company, New York [1988], p. 769) and can be used as signal sequences in appropriate eukaryotic host cells. Yeast signal sequences, as for example acid phosphatase (Arima et al., *Nuc. Acids Res.*, 11:1657 [1983]), alpha-factor, alkaline phosphatase and invertase may be used to direct secretion from yeast host cells. Prokaryotic signal sequences from genes encoding, for example, LamB or OmpF (Wong et al., *Gene* 68:193 1988]), MalE, PhoA, or beta-lactamase, as well as other genes, may be used to target proteins from prokaryotic cells into the culture medium.

An alternative technique to provide a protein of interest with a signal sequence such that it may be secreted is to chemically synthesize the DNA encoding the signal sequence. In this method, both strands of an oligonucleotide encoding the selected signal sequence are chemically synthesized and then annealed to each other to form a duplex. The double-stranded oligonucleotide is then ligated to the 5' end of the DNA encoding the protein.

The construct containing the DNA encoding the protein with the signal sequence ligated to it can then be ligated into a suitable expression vector. This expression vector is transformed into a an appropriate host cell and the protein of interest is expressed and secreted.

D. Transformation Methods

Cultures of mammalian host cells and other host cells that do not have rigid cell membrane barriers are usually transformed using the calcium phosphate method as originally described by Graham and Van der Eb (*Virology*, 52:546 [1978]) and modified as described in sections 16.32–16.37 of Sambrook et al. supra. However, other methods for introducing DNA into cells such as Polybrene (Kawai and Nishizawa, *Mol. Cell. Biol.*, 4:1172 [1984]), protoplast fusion (Schaffner, *Proc. Natl. Acad. Sci. USA*, 77:2163 [1980]), electropotation (Neumann et al., *EMBO J.*, 1:841 [1982]), and direct microinjection into nuclei (Capecchi, *Cell*, 22:479 [1980]) may also be used.

Yeast host cells are generally transformed using the polyethylene glycol method, as described by Hinnen (*Proc. Natl. Acad. Sci.* U.S.A., 75:1929 [1978]).

Prokaryotic host cells or other host cells with rigid cell walls are preferably transformed using the calcium chloride method as described in section 1.82 of Sambrook et al., supra. Alternatively, electropotation may be used for transformation of these cells.

E. Cloning Methods

Construction of suitable vectors containing DNA encoding replication sequences, regulatory sequences, phenotypic selection genes and the foreign DNA of interest are prepared using standard recombinant DNA procedures. Isolated plasmids and DNA fragments are cleaved, tailored, and ligated together in a specific order to generate the desired vectors.

The DNA is cleaved using the appropriate restriction enzyme or enzymes in a suitable buffer. In general, about 0.2–1 µg of plasmid or DNA fragments is used with about 1–2 units of the appropriate restriction enzyme in about 20.1 µl of buffer solution. (Appropriate buffers, DNA concentrations, and incubation times and temperatures are specified by the manufacturers of the restriction enzymes.) Generally, incubation times of about one or two hours at 37° C. are adequate, although several enzymes require higher temperatures. After incubation, the enzymes and other contaminants are removed by extraction of the digestion solution with a mixture of phenol and chloroform, and the DNA is recovered from the aqueous fraction by precipitation with ethanol.

To ligate the DNA fragments together to form a functional vector, the ends of the DNA fragments must be compatible with each other. In some cases the ends will be directly compatible after endonuclease digestion. However, it may be necessary to first convert the sticky ends, commonly produced by endonuclease digestion, to blunt ends to make them compatible for ligation. To blunt the ends, the DNA is treated in a suitable buffer for at least 15 minutes at 15° C. with 10 units of the Klenow fragment of DNA Polymerase I (Klenow) in the presence of the four deoxynucleotide triphosphates. It is then purified by phenolchloroform extraction and ethanol precipitation.

The cleaved DNA fragments may be size-separated and selected using DNA gel electrophoresis. The DNA may be electrophoresed through either an agarose or a polyacrylamide matrix. The selection of the matrix will depend on the size of the DNA fragments to be separated. After electrophoresis, the DNA is extracted from the matrix by electroelution, or, if low-melting agarose has been used as the matrix, by melting the agarose and extracting the DNA from it, as described in sections 6.30–6.33 of Sambrook et al., supra.

The DNA fragments that are to be ligated together (previously digested with the appropriate restriction enzymes such that the ends of each fragment to be ligated are compatible) are present in solution in about equimolar amounts. The solution will also contain ATP, ligase buffer and a ligase such as T4 DNA ligase at about 10 units per 0.5 μg of DNA. If the DNA fragment is to be ligated into a vector, the vector is first linearized by cutting with the appropriate restriction endonuclease(s) and then phosphatased with either bacterial alkaline phosphatase or calf intestinal alkaline phosphatase. This prevents self-ligation of the vector during the ligation step.

After ligation, the vector with the foreign gene now inserted is transformed into a suitable host cell, most commonly a prokaryote such as E. coli K12 strain 294 (ATCC number 31,446) or another suitable E. coli strain. The transformed cells are selected by growth on an antibiotic, commonly tetracycline (tet) or ampicillin (amp), to which they are rendered resistant due to the presence of tet and/or amp resistance genes on the vector. If the ligation mixture has been transformed into a eukaryotic host cell, transformed cells may be selected by the DHFR/MTX system described above. The transformed cells are grown in culture and the plasmid DNA (plasmid refers to the vector ligated to the foreign gene of interest) is then isolated. This plasmid DNA is then analyzed by restriction mapping and/or DNA sequencing. DNA sequencing is generally performed by either the method of Messing et al., *Nucleic Acids Res.,* 9:309 (1981) or by the method of Maxam et al., *Methods of Enzymology,* 65:499 (1980).

After mammalian host cells have been stably transformed with the DNA, the DHFR-protein-coding sequences are amplified by growing the host cell cultures in the presence of approximately 200–500 nM of methotrexate. The effective range of concentrations of MTX is highly dependent upon the nature of the DHFR gene and protein and the characteristics of the host. Clearly, generally defined upper and lower limits cannot be ascertained. Suitable concentrations of other folic acid analogs or other compounds that inhibit DHFR may also be used. MTX itself is, however, convenient, readily available, and effective.

As discussed above, t-PA variants are preferably produced by means of mutation(s) that are generated using the method of site-specific mutagenesis. This method requires the synthesis and use of specific oligonucleotides that encode both the sequence of the desired mutation and a sufficient number of adjacent nucleotides to allow the oligonucleotide to stably hybridize to the DNA template.

F. Pharmaceutical Compositions

The compounds of the present invention can be formulated according to known methods to prepare pharmaceutically useful compositions, whereby the t-PA product is combined in admixture with a pharmaceutically acceptable carrier. Suitable carriers and their formulations are described in *Remington's Pharmaceutical Sciences,* 16th ed., 1980, Mack Publishing Co., edited by Oslo et al., specifically incorporated by reference. These compositions will typically contain an effective amount of the t-PA variant, for example, from on the order of about 0.5 to about 5 mg/ml, together with a suitable amount of carrier to prepare pharmaceutically acceptable compositions suitable for effective administration to the patient. The t-PA variant may be administered parenterally to patients suffering from cardiovascular diseases or conditions, or by other methods that ensure its delivery to the bloodstream in an effective form.

Compositions, particularly well suited for the clinical administration of the t-PA variants used to practice this invention include sterile aqueous solutions or sterile hydratable powders such as lyophilized protein. Typically, an appropriate amount of a pharmaceutically acceptable salt is also used in the formulation to render the formulation isotonic. A buffer such as arginine base in combination with phosphoric acid is also typically included at an appropriate concentration to maintain a suitable pH, generally from 5.5 to 7.5. In addition, a compound such as glycerol may be included in the formulation to help maintain the shelf-life.

Dosages and desired drug concentrations of pharmaceutical compositions of this invention may vary depending on the particular use envisioned. For example, in the treatment of deep vein thrombosis or peripheral vascular disease, "bolus" doses, on the order of about 0.05 to about 0.2 mg/kg, will typically be preferred with subsequent administrations of on the order of about 0.1 to about 0.2 mg/kg administered to maintain a fairly constant blood level, preferably of on the order of about 3 μg/ml.

However, for use in connection with emergency medical care facilities where infusion capability is generally not available and due to the generally critical nature of the underlying disease (e.g., embolism, infarct), it is usually desirable to provide larger initial doses, such as an intravenous bolus of on the order of about 0.3 mg/kg.

For example, the t-PA variant is suitably administered parenterally to subjects suffering from cardiovascular diseases or conditions. Dosage and dose rate may be parallel to or higher than that currently in use in clinical investigations of other cardiovascular, thrombolytic agents, e.g., about 1–2 mg/kg body weight as an intravenous or intra-arterial dose over 1.5 to 12 hours in human patients suffering from myocardial infarction, pulmonary embolism, etc.

As one example of an appropriate dosage form, a vial containing 50 mg t-PA, arginine, phosphoric acid, and polysorbate 80 is reconstituted with 50 ml sterile water for injection and mixed with a suitable volume of 0.9 percent sodium chloride injection.

The t-PA variants of this invention are also useful for preventing fibrin deposition or adhesion formation or reformation. One embodiment of this use is described in EPO 297,860 published Jan. 4, 1989, the disclosure of which is incorporated by reference. Generally, this type of treatment involves topical administration of a composition to a site of potential fibrin or adhesion formation wherein the composition comprises a therapeutically effective amount of the t-PA variant in a sparingly soluble form that is continuously released at that site for a period of time of about from three days to two weeks. Typically, the t-PA variant is administered at a dosage sufficient to prevent fibrin deposition or formation of adhesions following surgery, infection, trauma, or inflammation. Usually, this amount is from 0.02 mg/g of gel to 25 mg/g of gel, with preferred amounts from 0.20 mg/g gel to about 2.5 mg/g gel, most preferably from 0.25 mg/g gel to about 1.0 mg/g gel.

Each t-PA variant used to prevent adhesion formation and/or fibrin deposition is typically formulated in a semisolid, mucilagenous, pharmaceutically inert carrier for positioning the enzyme at the site of potential adhesion formation. The carrier includes long-chain hydrocarbons or vegetable oils and waxes composed of mixtures of modified saturated and unsaturated fatty acid glycerides or mixtures of modified saturated and unsaturated fatty acid glycerides. Examples include semisolid vehicles such as petroleum Jelly or semi-synthetic glycerides, polyhydroxy solvents such as glycerol, long-chain hydrocarbons, bioerodable polymers, or liposomes.

The decreased clearance rate of the t-PA variants of this invention may render them suitable for rapid intravenous injection, particularly as a bolus, for example. This would simplify the method of administration of t-PA and might permit the use of t-PA in situations where medical equipment is limited, such as in emergency vehicles staffed with paramedic personnel. In addition, the extended clearance rate of these t-PA variants may also permit administration of lower initial doses and/or low-dose extended therapy that may be necessary to avoid reocclusion following acute thrombolysis, or for extended thrombolysis that may be necessary in cases of peripheral vascular occlusion.

In order to simplify the examples certain commonly used methods are referenced by the phrases below.

"Plasmids" are designated by a lower case p followed by an alphanumeric designation. The starting plasmids used in this invention are either commercially available, publicly available on an unrestricted basis, or can be constructed from such available plasmids using published procedures. In addition, other equivalent plasmids are known in the art and will be apparent to the ordinary artisan.

"Digestion" "cutting" or "cleaving" of DNA refers to catalytic cleavage of the DNA with an enzyme that acts only at particular locations in the DNA. These enzymes are called restriction endonucleases, and the site along the DNA sequence where each enzyme cleaves is called a restriction site. The restriction enzymes used in this invention are commercially available and are used according to the instructions supplied by the manufacturers. Restriction enzymes are designated by abbreviations composed of a capital letter followed by two or three lower case letters representing the microorganism from which each restriction enzyme was obtained. These letters are followed by one or more Roman numerals that identify the particular enzyme. In general, about 1 µg of plasmid or DNA fragment is used with about 2 units of enzyme in about 20 µl of buffer solution. The appropriate buffer, substrate concentration, incubation temperature, and incubation time for each enzyme is specified by the manufacturer. After incubation, the enzyme and other contaminants are removed from the DNA by extraction with a solution of phenol-chloroform, and the digested DNA is recovered from the aqueous fraction by precipitation with ethanol. Digestion with a restriction enzyme may be followed by treatment with bacterial alkaline phosphatase or calf intestinal alkaline phosphatase. This prevents the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. These procedures and reagents for dephosphorylation are described in sections 1.60-1.61 and sections 3.38-3.39 of Sambrook et al., supra.

"Recovery" or "isolation" of a given fragment of DNA from a restriction digest means separation of the resulting DNA fragment on a polyacrylamide or an agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn et al., 1981, *Nucleic Acids Res.* 9:6103-6114, and D. Goeddel et al., 1980, *Nucleic Acids Res.* 8:4057.

"Southern Analysis" is a method by which the presence of DNA sequences in a digest or DNA-containing composition is confirmed by hybridization to a known, labelled oligonucleotide or DNA fragment. Southern analysis refers to the separation of digested DNA on an agarose gel, denaturation of the DNA, and transfer of the DNA from the gel to a nitrocellulose or nylon membrane using methods originally described by Southern (*J. Mol. Biol.*, 98:503 [1975]) and modified as described in sections 9.31-9.57 of Sambrook et al., supra.

"Transformation" means introducing DNA into an organism so that the DNA is replicable, either as an extrachromosomal element or chromosomal integrant. The method used for transformation depends on whether the host cell is a eukaryote or a prokaryote. The method used to transform prokaryotes is the calcium chloride method as described in section 1.82 of Sambrook et al., supra. Eukaryotes are transformed using the calcium phosphate method as described in sections 16.32-16.37 of Sambrook et al , supra "Ligation" refers to the process of forming phosphodiester bonds between two double stranded DNA fragments using the enzyme ligase in a suitable buffer that also contains ATP.

"Oligonucleotide" refers to short length single or double stranded sequences of deoxyribonucleotides linked via phosphodiester bonds. The oligonucleotides are chemically synthesized by known methods and purified on polyacrylamide gels.

The following examples merely illustrate the best mode now contemplated for practicing the invention, but should not be construed to limit the invention. All literature citations herein are expressly incorporated by reference.

EXAMPLE I

A strategy known as alanine-scanning mutagenesis (ALA-scan), described in Cunningham and Wells, supra, was used to construct the t-PA variants. This method involved the identification of small regions of the t-PA molecule that contain charged amino acid side chains. Without limitation to any one theory, it is believed that either these regions containing clusters of charge, or neighboring regions, or both, are responsible for the interaction of the t-PA molecule with its substrate and various other compounds that may modulate its activity. Some of the charged amino acids in each region (i.e., Arg, Asp, His, Lys, and Glu) were replaced with alanine to assess the importance of the particular region to the overall clearance rate of the t-PA molecule.

I. Construction of the Expression Vector pRK.t-PA

Figure 1:
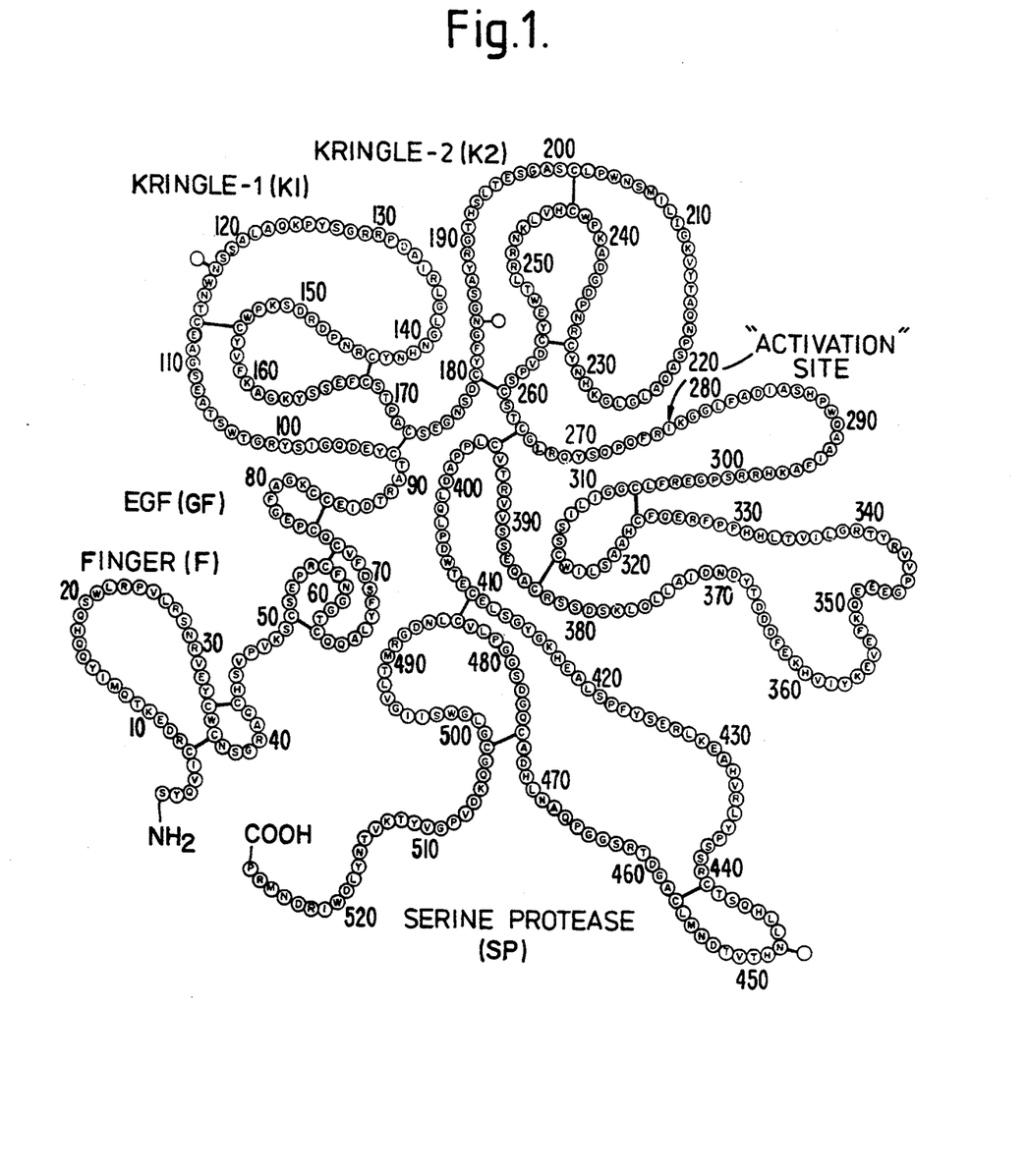
FIG. 1 depicts the amino acid sequence of the mature form of human t-PA. The amino acids are numbered starting from the amino terminus. The five domains, disulfide bridging, and the activation site where the molecule is clipped into the two-chain form are indicated.
Figure 2:
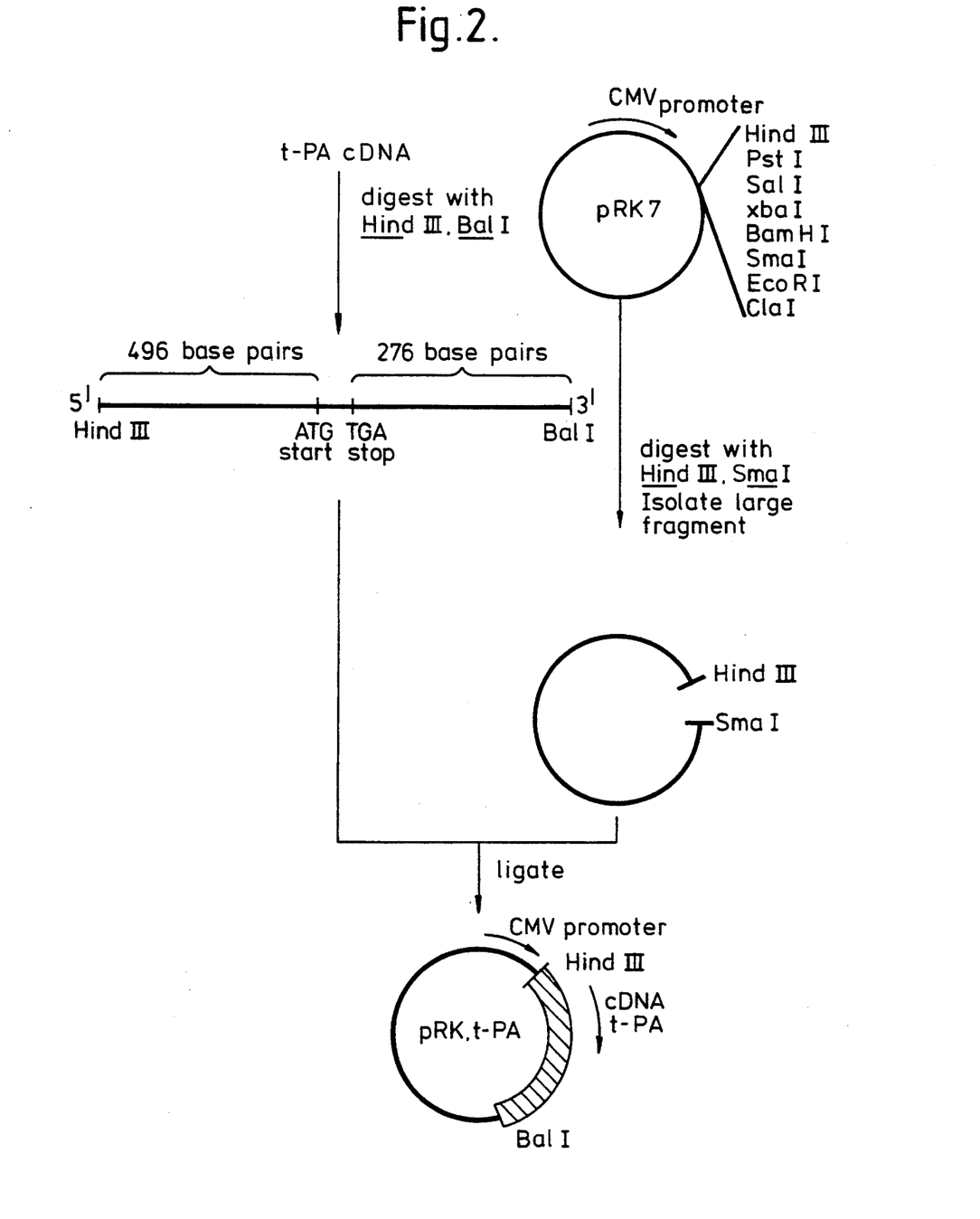
FIG. 2 diagrams the construction of pRK.t-PA. The human t-PA cDNA was digested with HindIII and BalI and inserted into the eukaryotic expression vector pRK7 between the HindIII and SmaI sites.

Plasmid pRK7 was used as the vector for generation of the t-PA mutants. pRK7 is identical to pRK5 (EP Publication Number 307,247 published Mar. 15, 1989), except that the order of the endonuclease restriction sites in the polylinker region between ClaI and HindIII is reversed. The t-PA cDNA (Pennica et al., *Nature*, 301:214 [1983]) was prepared for insertion into the vector by cutting with restriction endonuclease HindIII (which cuts 496 base pairs 5' of the ATG start codon) and restriction endonuclease BalI (which cuts 276 base pairs downstream of the TGA stop codon). This cDNA was ligated into pRK7 previously cut with HindIII and SmaI using standard ligation procedures as described in sections 1.68–1.69 of Sambrook et al., supra. This construct was named pRK.t-PA.

II. site Directed Mutagenesis of pRK7-t-PA

Site-directed mutagenesis of t-PA cDNA was performed by the method of Taylor et al. (*Nucl. Acids. Res.*, 13:8765 [1985]) using a kit purchased from the Amersham Corporation (catalog number RPN 1253). For generation of the desired mutants, oligonucleotides of sequences coding for the desired amino acid substitutions were synthesized and used as primers. These oligonucleotides were annealed to single-stranded pRK7-t-PA that had been prepared by standard procedures (Viera et al., *Meth. Enz.*, 143:3 [1987]).

A mixture of three deoxyribonucleotides, deoxyriboadenosine (dATP), deoxyriboguanosine (dGTP), and deoxyribothymidine (dTTP), was combined with a modified thio-deoxyribocytosine called dCTP(aS) provided in the kit by the manufacturer of the kit, and added to the single-stranded pRK7-t-PA to which was annealed the oligonucleotide.

Upon addition of DNA polymerase to this mixture, a strand of DNA identical to pRK7-t-PA except for the mutated bases was generated. In addition, this new strand of DNA contained dCTP(aS) instead of dCTP, which served to protect it from restriction endonuclease digestion. After the template strand of the double-stranded heteroduplex was nicked with an appropriate restriction enzyme, the template strand was digested with ExoIII nuclease past the region that contained the mutagenic oligomer. The reaction was then stopped to leave a molecule that was only partly single-stranded. A complete double-stranded DNA homoduplex molecule was then formed by DNA polymerase in the presence of all four deoxyribonucleotide triphosphates, ATP, and DNA ligase.

The oligonucleotides listed in Table A were synthesized for use as primers to generate the pRK7-t-PA variants, also listed in Table A, using the ALA-scan methodology described above:

TABLE A

| Variant | Oligonucleotide |
|---|---|
| *E94A | 5' GCCCTGGTCCGCGTAGCACGTGGC 3' |
| *D95A | 5' GATGCCCTGCGCCTCGTAGCACGT 3' |
| *D95G | 5' GATGCCCTGGCCCTCGTAGCACGT 3' |
| *E94A, D95A | 5' GATGCCCTGGGCCGCGTAGCACGT 3' |
| *D236A, D238A, K240A | 5' GGCACCAGGGCGCGGCAGCCCCAGCAGGATTCCG 3' |
| T103N | 5' TGTGCTCCAATTGCCCCTGTAGCT 3' |
| N117Q | 5' CAACGCGCTGCTTTGCCAGTTGGT 3' |

The asterisks indicate variants that are illustrative of this invention.

Although the variants E94A,D95A and D236A,D238A,K240A are actually multiple mutants, as they contain more than one amino acid substitution, they were each generated using only one oligonucleotide. This was possible since the substituted amino acids are located very close to each other in the polypeptide chain.

A slight variation of the above described procedure was employed to prepare additional multiple mutants illustrative of this invention. For these mutants, described below, the template DNA was not wild-type t-PA (pRK7.t-PA). Instead, the templates used were those that contained at least a single mutation, i.e., the DNA produced in construction of the single mutants listed above. The DNA used as the template, and the oligonucleotide used to generate the additional mutation(s) for each multiple mutant made is listed in Table B below. The DNA sequence of each oligonucleotide is set forth in Table A above.

TABLE B

| Multiple Mutant | DNA Template | Oligonucleotide |
|---|---|---|
| *E94A, D95A, T103N | E94A, D95A | T103N |
| *E94A, D95A, N117Q | E94A, D95A | N117Q |
| *E94A, D95A, D236A, D238A, K240A | D236A, D238A, K240A | E94A, E95A |
| T103N, N117Q | T103N | N117Q |
| *T103N, D236A, D238A, K240A | T103N | D236A, D238A, K240A |
| *N117Q, D236A, D238A, K240A | N117Q | D236A, D238A, K240A |

The asterisks indicate variants that are illustrative of this invention.

III. Bacterial Transformation and DNA Preparation

The mutant t-PA constructs generated using the protocol above were transformed into *E. coli* host strain MM294tonA using the standard calcium chloride procedure (sections 1.76–1.84 of Sambrook et al., supra) for preparation and transformation of competent cells. The *E. coli* strain MM294tonA (which is resistant to T1 phage) was prepared by the insertion and subsequent imprecise excision of a Tn10 transposon into the tonA gene. This gene was then inserted, using transposon insertion mutagenesis (Kleckner et al., *J. Mol. Biol.*, 116:125–159 [1977]), into *E. coli* host MM294 (ATCC 31,446).

DNA was extracted from individual colonies of bacterial transformants using the standard miniprep procedure described in sections 1.25–1.31 of Sambrook et al., supra. The plasmids were further purified by passage over a Sephacryl CL6B spin column, and then analyzed by DNA sequencing and by restriction endonuclease digestion and agarose gel electrophoresis.

IV. Transformation of Eukaryotic Cells

Human embryonic kidney 293 cells were grown to 70% confluence in 6-well plates. 2.5 μg of plasmid encoding the t-PA mutant was dissolved in 150 μl of i mM Tris-HCl, 0.1 mM EDTA, 0.227M CaCl$_2$. Added to this (dropwise while vortexing) was 150 μl of 50 mM HEPES buffer (pH 7.35), 280 mM NaCl, 1.5 mM NaPO$_4$, and the precipitate was allowed to form for ten min. at 25° C. The suspended precipitate was then added to the cells in the individual wells in a 6-well plate and allowed to settle for four hours in the incubator. The medium was then aspirated off and I ml of 20% glycerol in PBS (phosphate buffered saline) was added. The cells were washed twice, first with 3 ml, then with I ml, of serum-free medium. Then 3 ml of fresh medium was added and the cells were incubated for five days. The medium was then collected and assayed.

When single-chain t-PA was required, the procedure was as described above except that plasminogen-depleted serum was used during the growth phase of the cells.

V. Biological Assays

A. t-PA Quantitation

The concentration of t-PA in the cell culture supernatants was determined by the ELISA (enzyme linked immunosorbent assay) procedure using polyclonal antibodies prepared against wild-type t-PA. The amount of t-PA used in each assay described below was based on the results of this ELISA procedure.

B. S-2288 Assay

The S-2288 assay was used to measure the proteolytic activity of the mutants in the two-chain form. This assay is a direct assay for t-PA proteolytic activity; t-PA cleaves the bond between the small peptide and the paranitroanilide chromophore.

Standard curve samples were prepared by diluting wild-type recombinant t-PA (rt-PA) with cell culture media. The standard curve samples and rt-PA mutant samples were added to the wells of a microtiter plate. Since the assay was used to measure the activity of two-chain rt-PA, an incubation step with human plasmin was included in the procedure. Human plasmin (KabiVitrum) was added to a final concentration of 0.13 CU (casein units)/ml. The samples were incubated for 90 minutes at room temperature.

Aprotinin [Sigma, approximately 14 TIU (trypsin inhibitor unit)/mg] was added to a final concentration of 72 $\mu$g/ml to inhibit the plasmin activity, and the samples were incubated at room temperature for 15 minutes. A 2.16 mM solution of S-2288 was diluted to 1.45 mM with 0.1M Tris, 0.106 mM NaCl, 0.02% sodium azide pH 8 4 and 100 $\mu$l of this solution was added to each well of the microtiter plate (final volume in each well was 200 $\mu$l). Color development was monitored at 405 nm. The slope of the absorbance vs. time curve for each standard and sample was determined. A standard curve was prepared by plotting the slope of the absorbance vs. time curve as a function of rt-PA concentration for the rt-PA standards. The relative activity concentration of the mutants was then determined from the standard curve. The activity concentration of each mutant was divided by the concentration for the mutant obtained in the rt-PA ELISA, and the resulting specific activities were expressed relative to wild-type t-PA, which was assigned a value of 1.0.

C. S-2251 Assay

This assay is an indirect assay for t-PA activity. In this assay, plasminogen is converted to plasmin by the action of t-PA, and plasmin cleaves the S-2251 substrate to release the paranitroanilide chromophore. Production of this chromophore is then measured over time.

1. Fibrin-Stimulated S-2251 Assay

Standard curve samples were prepared as described for the S-2288 assay. Conversion of the samples to the two chain form was accomplished by incubating them with plasmin-Sepharose. Plasmin-Sepharose was prepared by coupling approximately 20.8 CU of human plasmin (KabiVitrum) to 1 ml of cyanogen bromide activated Sepharose (Pharmacia). The plasmin-Sepharose (50.1 of a 5% 15 slurry) was incubated with shaking for 90 min. at room temperature with 150 $\mu$l of sample. Following the incubation, the resin was removed by centrifugation, and 10 $\mu$l of sample were added to the wells of a microtiter plate.

Human thrombin (10 $\mu$l of a 42 unit/ml solution) was added to each well. The reaction in each well was started by the addition of a cocktail (130 $\mu$l) composed of 28 $\mu$l of human Glu-plasminogen (5.3 $\mu$M); 10.1 $\mu$l of plasminogen-free human fibrinogen (10 $\mu$M); 30 $\mu$l of 3mM S-2251 (KabiVitrum); and 62 $\mu$l of PBS. Color development was monitored at 405 nm, and the absorbance at the reference wavelength of 492 nm was subtracted from each time point. The slope of the absorbance vs. time squared curve was determined for each standard and mutant sample. A standard curve was prepared by plotting the slope of the absorbance vs. time squared curve as a function of rt-PA concentration for the rt-PA standards. The determination of the relative specific activity for the mutants was as described for the S-2288 assay.

2. Fibrinogen Stimulated S-2251 Assay

This assay was performed as described for the fibrin-stimulated S-2251 assay except that PBS was substituted for the thrombin.

3. Plasma Clot S-2251 Assay

The standard curve sample preparation and the conversion of one-chain rt-PA to two-chain rt-PA using plasmin-Sepharose were as described for the fibrin-stimulated S-2251 assay. Human thrombin (10 $\mu$l of a 31 $\mu$g/ml solution) was added to each well of the microtiter plate. The standard and mutant samples (40 $\mu$l) were added to the plate and the reaction was started by adding 100 $\mu$l of a mixture of 90 $\mu$l of acid citrate dextrose human plasma and 10 $\mu$l of 9.1 mM S-2251 (KabiVitrum). Color development was monitored at 405 nm and the absorbance at the reference wavelength of 492 nm was subtracted from each time point. The analysis of the data was as described for the fibrin-stimulated S-2251 assay.

The results of the assays described in sections B and C above are presented in Table 1, where the asterisks represent the mutants of this invention. The remaining mutants have been disclosed previously and are included for comparison.

The results of the S-2288 assay indicate that illustrative variants of this invention have an activity that is nearly equal to or greater than that of wild-type t-PA.

In the fibrin-stimulated S-2251 assay, the single mutants of this invention that are presented in Table i have an activity that similar to that of wild-type t-PA. The multiple mutants E94A,D95A,N117Q and N117Q,D236A,D238A,K240A have substantially higher activity than that of wild-type t-PA. Surprisingly, their activity was also found to he higher than that of any of the single mutants.

The results of the fibrinogen-stimulated S-2251 assay show that the activity of most of the single mutants herein was found to be similar to that of wild-type t-PA. Unexpectedly, the activity of two of the multiple mutants, E94A,D95A,N117Q and N117Q,D236A,D238A,K240A was found to be substantially higher than that of the single mutants.

In the plasma-clot S-2251 assay, most of the variants herein were found to have an activity comparable to that of wild-type t-PA.

TABLE 1

| t-PA Variant | S2251 in Plasma Clot | S2251 with Fibrin only | S2251 with Fibrinogen | S2288 Assay |
|---|---|---|---|---|
| Wild-type | 1.0 | 1.0 | 1.0 | 1.0 |
| *E94A | 0.90 | 0.79 | 0.74 | 0.78 |
| *D95A | 1.07 | 0.87 | 0.85 | 0.98 |
| *E94A, D95A | 0.91 | 0.86 | 0.83 | 0.91 |
| T103N | 0.67 | 0.80 | 0.47 | 0.93 |
| N117Q | 1.10 | 1.07 | 1.62 | 1.01 |
| *D236A, D238A, K240A | 1.01 | 0.87 | 0.83 | 0.97 |
| *E94A, D95A, T103N | 0.63 | 0.82 | 0.52 | 1.09 |
| *E94A, D95A, N117Q | 1.25 | 1.51 | 2.25 | 1.25 |
| *E94A, D95A, D236A, D238A, K240A | 0.67 | 1.06 | 0.40 | 1.95 |
| T103N, N117Q | 1.12 | 1.21 | 1.13 | 1.19 |
| *T103N, D236A, D238A, K240A | 0.64 | 0.66 | 0.52 | 1.12 |
| *N117Q, D236A, D238A, K240A | 1.23 | 1.24 | 1.55 | 1.31 |
| *D95G | 0.99 | 1.36 | 1.15 | 0.95 |

D. Plasma Clot

All t-PA variant samples were converted from the one-chain to the two-chain form using plasmin-Sepharose as described for the fibrin-stimulated S-2251 assay above.

The plasma clot lysis assay was performed as follows: 10 ml of 0.15M calcium chloride was added to microtiter plate wells. Each well then received 90 μl of centrifuged and 0.45-micron-filtered human citrated plasma pool. The contents were thoroughly mixed to form the plasma clot. Standard samples of rt-PA and the t-PA variants to be assayed were diluted in assay buffer to twice their final concentration (18–800 ng/ml). The dilution buffer consisted of 0.1M NaCl, 0.03M sodium bicarbonate (added fresh just prior to starting the experiment), 4 mM KCl, 1 mM calcium chloride, 1 mM dibasic sodium phosphate, 0.3 mM magnesium chloride, 0.4 mM magnesium sulfate, 20 mM HEPES (4-[2-hydroxyethyl]-1-piperazineethane sulfonic acid), and 0.01% Polysorbate 80, pH 7.4. Each standard or variant was then mixed with one volume of the plasma pool. A total of 100 μl of this mixture was then layered over the plasma clot after the clot had been allowed to sit at ambient temperature for 6–8 hours. The optical density of each plate was then read at 405 nm. The plate was then incubated at 37° C. for about 15 hours, and the optical density measurement was repeated. For each well the difference in optical density values from time 0 to 15 hours was calculated by subtraction. For the standards, the optical density was plotted as a function of the log of the concentration of the standard. Unknowns were interpolated from the standard curve. Normalization was to identically treated wild-type t-PA controls. Standard curves were determined using a four parameter fit program. The plate reader employed was from SLT-Laboratories, Model EAR340AT (Austria).

The results are shown in Table 2, where the asterisks denote the variants of this invention.

TABLE 2

| t-PA Variant | Clearance Ratio | Clot Lysis in Plasma |
|---|---|---|
| Wild-type | 1.0 | 1.0 |
| *E94A | 0.61 | 0.82 |
| *D95A | 0.38 | 0.97 |
| *E94A, D95A | 0.34 | 0.74 |
| T103N | 0.36 | 0.82 |
| N117Q | 0.44 | 0.66 |
| *D236A, D238A, K240A | 0.45 | 0.55 |
| *E94A, D95A, T103N | 0.17 | 0.57 |
| *E94A, D95A, N117Q | 0.23 | 0.70 |
| *E94A, D95A, D236A, D238A, K240A | 0.56 | 0.40 |
| T103N, N117Q | 0.27 | 0.86 |
| *T103N, D236A, D238A, K240A | 0.26 | 0.91 |
| *N117Q, D236A, D238A, K240A | 0.34 | 0.45 |
| *D95G | 0.37 | N/A |

N/A indicates that this data was not available

The single variants that are illustrative of this invention have activity in this assay comparable to that of wild-type t-PA and T103N, and activity that is better than that of N117Q. Certain 5 of the multiple variants are comparable in clot lysis activity to wild-type, including E94A,D95A,N117Q and T103N,D236A,D238A,K240A.

VI. clearance Rate Assay

Clearance was measured by injecting mice with 125-I-labeled t-PA, and monitoring the amount of radioactivity remaining in the bloodstream over time. The preparation of 125-I-labeled t-PA required several steps that are described below.

A. Radiolabeling of/t-PA Variants

The first step in the preparation of the radiolabeled t-PA variants was to radiolabel the reagent D-Tyr-Pro-Arg-chloromethylketone (YPRck, obtained from Bachem Bioscience, Inc., Philadelphia, Penn.) with 125-I. This reagent acts as a suicide substrate for t-PA by binding irreversibly to t-PA. The t-PA molecule thus becomes iodinated indirectly through the covalent bond formed with YPRck.

The YPRck reagent was radiolabeled by Chloramine T catalyzed iodination using a method based on that described by Hunter and Greenwood (Nature, 194:495 [1962]). In a typical reaction, 50 μl of 1M Tris-HCl at pH 7.5 was added to 40 μl of sodium iodide-125 (4 milliCuries, 1.8 nmol) in a capped reaction vessel. To this reaction was added 8.3 μl of YPRck reagent (0.83 μg, 1.8 nmol) which had been prepared as a stock solution of 100μg/ml in 12 mM HCl. The resulting mixture was a 1:1 stoichiometric mixture of sodium iodide and YPRck. The iodination reaction was initiated by addition of 12.5 μl of 1 mg/ml Chloramine T in 0.1M sodium phosphate at pH 7.5. After 60 seconds, the iodination reaction was terminated by addition of 25 μl of 1 mg/ml sodium metabisulfite in 0.1M sodium phosphate at pH 7.5. The reaction vessel was vortexed after each addition. Immediately following the iodination of YPRck, 2 mls of PBS with 0.01% Tween-20 was added to the reaction vessel and vortexed to dilute the radioactive label.

Cell culture supernatants were collected from 293 cells that had been transformed six days earlier with DNA encoding the t-PA variants. These cells were actively secreting the variant t-PA proteins, and the cell culture medium typically contained about 1 μg/ml of t-PA. Twenty microliters of the diluted YPRck-125-I reagent was added to 900 μl of cell culture supernatant. This mixture was incubated at 25° C. for 1 hour and then applied to a Sephadex G-25 column previously equilibrated with 0.1% gelatin in PBS with 0.003 % Tween-20. One milliliter fractions were collected from each column, and the fourth fraction routinely contained about 85% of the total protein bound radioactivity, as determined by trichloroacetic acid precipitation of an aliquot of each fraction.

B. Pharmacokinetic Assay

Figure 3:
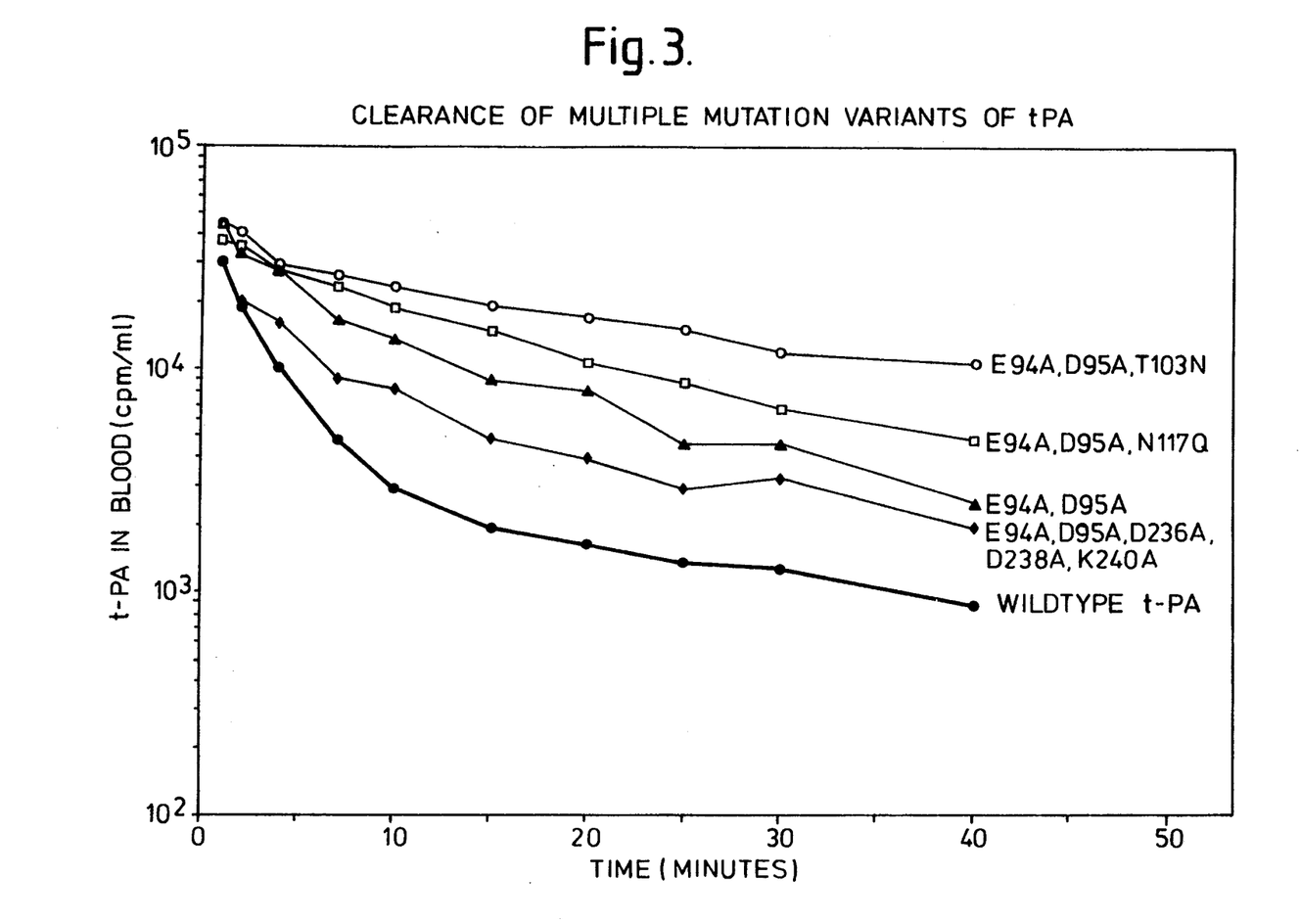
FIG. 3 is a plot of the amount of radiolabeled t-PA variant remaining in the bloodstream of mice (measured in thousands of counts per minute per ml of blood) versus time (in minutes). Radiolabelled t-PA variants were typically 1000 cpm per nanogram of protein. Each variant assayed is indicated, as is wild-type t-PA.

The following assay was used to calculate the clearance rate of YPRck-labeled t-PA variants in mice. Four mice were used to assess each variant. The YPRck-labeled-t-PA variants were diluted to a concentration of 1 million cpm/ml. Each mouse was injected the tail with 100 μl of YPRck-labeled-t-PA in a solution of PBS containing 0.5% BSA and 0.01% Tween 20. The mice were tail-bled pairs. The first pair was bled 1, 4, 10, 20, and 30 minutes after the initial injection. The second pair was bled 2, 7, 15, 25, and 40 minutes after the initial injection. An aliquot of 70 μl of blood was precipitated in 10% trichloroacetic acid (TCA). The TCA precipitable material was counted using a gamma scintillation counter and representative results were plotted on a graph, as shown in FIG. 3. The area under the curve (AUC) for each mouse was then calculated. Clearance rate was then determined using the formula: Clearance=Dose/AUC. The clearance rates from the blood of the mice that received t-PA variants were normalized to that of wild-type t-PA (clearance rate of wild-type t-PA divided by clearance rate of the variant).

The results of this assay are presented as clearance ratios and are shown above in Table 2. Illustrative t-PA variants of this invention have a clearance ratio that is less than that of wild-type t-PA. This indicates that the variants have a decreased clearance as compared to wild-type t-PA. Some of the double and triple mutants had a lower clearance ratio than the single mutants. The mutants T103N,D236A,D238A,K240A; N117Q,D236A,D238A,K240A; E94A,D95A,T103N; and E94A,D95A,N117Q all displayed lower clearance ratios than the single mutants at any one of these positions.

We claim:

1. A human tissue plasminogen activator (t-PA) amino acid sequence variant having an alternation consisting essentially of the substitution of
   a) a naturally occurring L-alpha-amino acid at at least one of amino acid positions 94 and 95, or
   b) alanine or glycine at each of amino acid positions 236, 238, and 240, or
   c) a naturally occurring L-alpha-amino acid at each of amino acid positions 94 and 95 in combination with either the substitution of either alamine or glycine at each of amino acid positions 236, 238 and 240, or with the substitution of alanine at each of amino acid positions 296, 297, 298 and 299, or
   d) a naturally occurring L-alpha amino acid at each of amino acid positions 94 and 95, or alanine or glycine at each of amino acid positions 236, 238 and 240 in combination with either the substitution of asparagine at amino acid position 103, or with the substitution of glutamine at amino acid position 117 of wild-type human t-PA,
   wherein each of amino acid positions 236, 238 and 240 is substituted with the same amino acid, and wherein said variant is capable of converting plasminogen to plasmin and has a decreased clearance from the bloodstream as compared to wild-type human t-PA.

2. The variant of claim 1 wherein glutamic acid at position 94 of wild-type human t-PA is substituted with alanine or glycine.

3. The variant of claim 2 additionally substituted with asparagine at position 103.

4. The variant of claim 2 additionally substituted with glutamine at position 117.

5. The variant of claim 1 wherein aspartic acid at position 95 of wild-type human t-PA is substituted with any naturally occurring L-alpha amino acid amino acid.

6. The variant of claim 5 wherein position 95 is substituted with alanine or glycine.

7. The variant of claim 5 additionally substituted with asparagine at position 103.

8. The variant of claim 5 additionally substituted with glutamine at position 117.

9. The variant of claim 1 wherein glutamic acid at amino acid position 94 is substituted with alanine or glycine and aspartic acid at amino acid position 95 is substituted with any naturally occurring L-alpha amino acid.

10. The variant of claim 9 wherein position 94 is substituted with alanine or glycine and position 95 is substituted with alanine or glycine.

11. The variant of claim 10 additionally substituted with alanine or glycine at each of amino acid positions 236, 238, and 240.

12. The variant of claim 1 wherein alanine is substituted for each of aspartic acid at amino acid positions 236 and 238, and for the lysine at amino acid position 240 of wild-type human t-PA.

13. The variant of claim 12 additionally substituted with glutamine at position 117.

14. The variant of claim 12 additionally substituted with asparagine at position 103.

15. A composition for treating a vascular condition or disease comprising a therapeutically effective amount of the variant of claim 1 in admixture with a pharmaceutically acceptable carrier.

16. A method for treating a vascular condition or disease in a mammal comprising administering an effective amount of the composition of claim 15 to the mammal.

17. A human tissue plasminogen activator (t-PA) variant selected from the group consisting of E94A t-PA; D95X t-PA; E94A, D95A t-PA; D236A,D238A,K240A t-PA; E94A,D95A,T103N t-PA; E94A,D95A,N117Q t-PA; E94A,D95A,D236A,D238A,K240A t-PA; T103N,D236A,D238A,K240A t-PA; and N117Q,D236A,D238A,K240A t-PA, wherein X is a naturally occurring L-alpha amino acid.

* * * * *